United States Patent [19]

Ebling et al.

[11] Patent Number: 4,934,340
[45] Date of Patent: Jun. 19, 1990

[54] DEVICE FOR GUIDING MEDICAL CATHETERS AND SCOPES

[75] Inventors: Wendel V. Ebling, El Toro; Richard L. Quick, Trabuco Canyon, both of Calif.

[73] Assignee: Hemo Laser Corporation, Irvine, Calif.

[21] Appl. No.: 364,069

[22] Filed: Jun. 8, 1989

[51] Int. Cl.⁵ ............................................. A61B 1/06
[52] U.S. Cl. ........................................ 128/6; 128/4; 604/95
[58] Field of Search .................. 128/4, 6, 772; 604/95

[56] References Cited

U.S. PATENT DOCUMENTS

| | | | |
|---|---|---|---|
| 3,043,309 | 7/1962 | McCarthy | 128/348 |
| 3,605,725 | 9/1971 | Bentov | 128/2.05 R |
| 3,674,014 | 7/1972 | Tillander | 128/2.05 R |
| 3,729,008 | 4/1973 | Berkovits | 128/418 |
| 3,773,034 | 11/1973 | Burns et al. | 128/2 M |
| 3,890,977 | 6/1975 | Wilson | 128/418 |
| 4,033,331 | 7/1977 | Guss et al. | 128/2 M |
| 4,146,019 | 3/1979 | Bass et al. | 128/6 |
| 4,176,662 | 12/1979 | Frazer | 128/6 |
| 4,456,017 | 6/1984 | Miles | 128/772 |
| 4,543,090 | 9/1985 | McCoy | 604/95 |
| 4,586,923 | 5/1986 | Gould et al. | 604/95 |
| 4,601,283 | 7/1986 | Chikama | 128/4 |
| 4,601,705 | 7/1986 | McCoy | 604/95 |
| 4,742,817 | 5/1988 | Kawashima et al. | 128/4 |
| 4,753,223 | 6/1988 | Bremer | 128/4 |
| 4,758,222 | 7/1988 | McCoy | 604/95 |
| 4,790,624 | 12/1988 | Van Hoye et al. | 128/4 X |
| 4,799,474 | 1/1989 | Ueda | 128/4 |

Primary Examiner—William H. Grieb
Attorney, Agent, or Firm—Stetina and Brunda

[57] ABSTRACT

Disclosed is a "bending assembly" which, when positioned with a flexible catheter, cannula, scope, or the like, is operative to cause periodic bending of the catheter, cannula, scope, or the like so as to assist in guiding the catheter, cannula, scope, or the like through curved or branched anatomical structures. The bending assembly comprises (a) a contractile wire or member, (b) a bendable support means, and (c) a connecting member linking the contractile wire to the bendable support means. When electrical current is passed through the contractile wire, it will undergo axial shortening, thereby causing the bendable support means to bend in the direction of the contractile wire with resultant movement or bending of the catheter, cannula, scope, or the like in which the bending assembly is disposed.

47 Claims, 2 Drawing Sheets

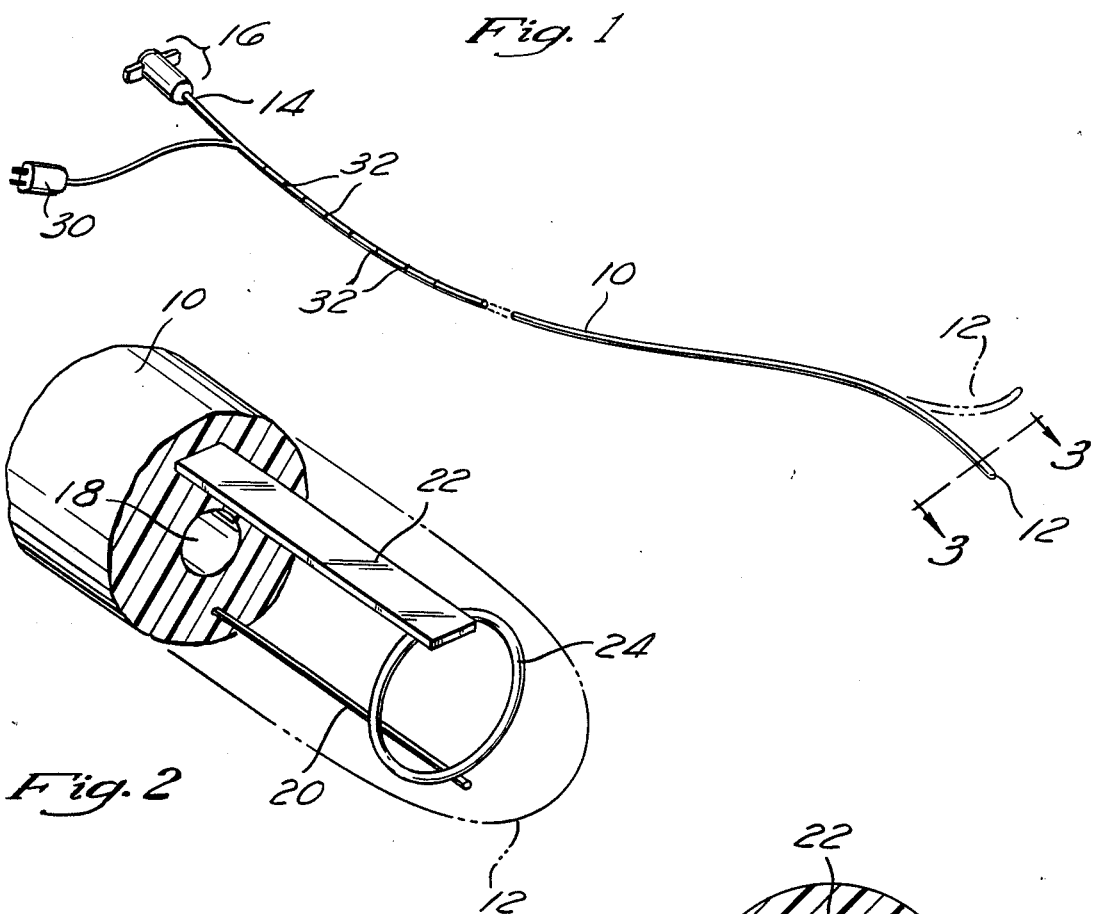
Fig. 1
Fig. 2
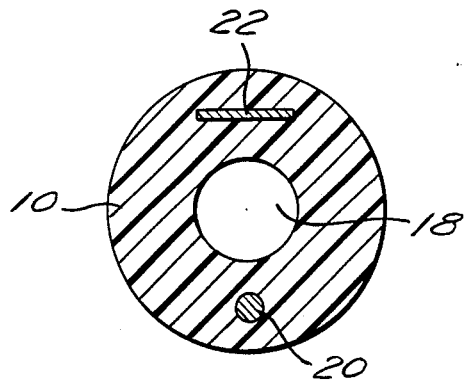
Fig. 3

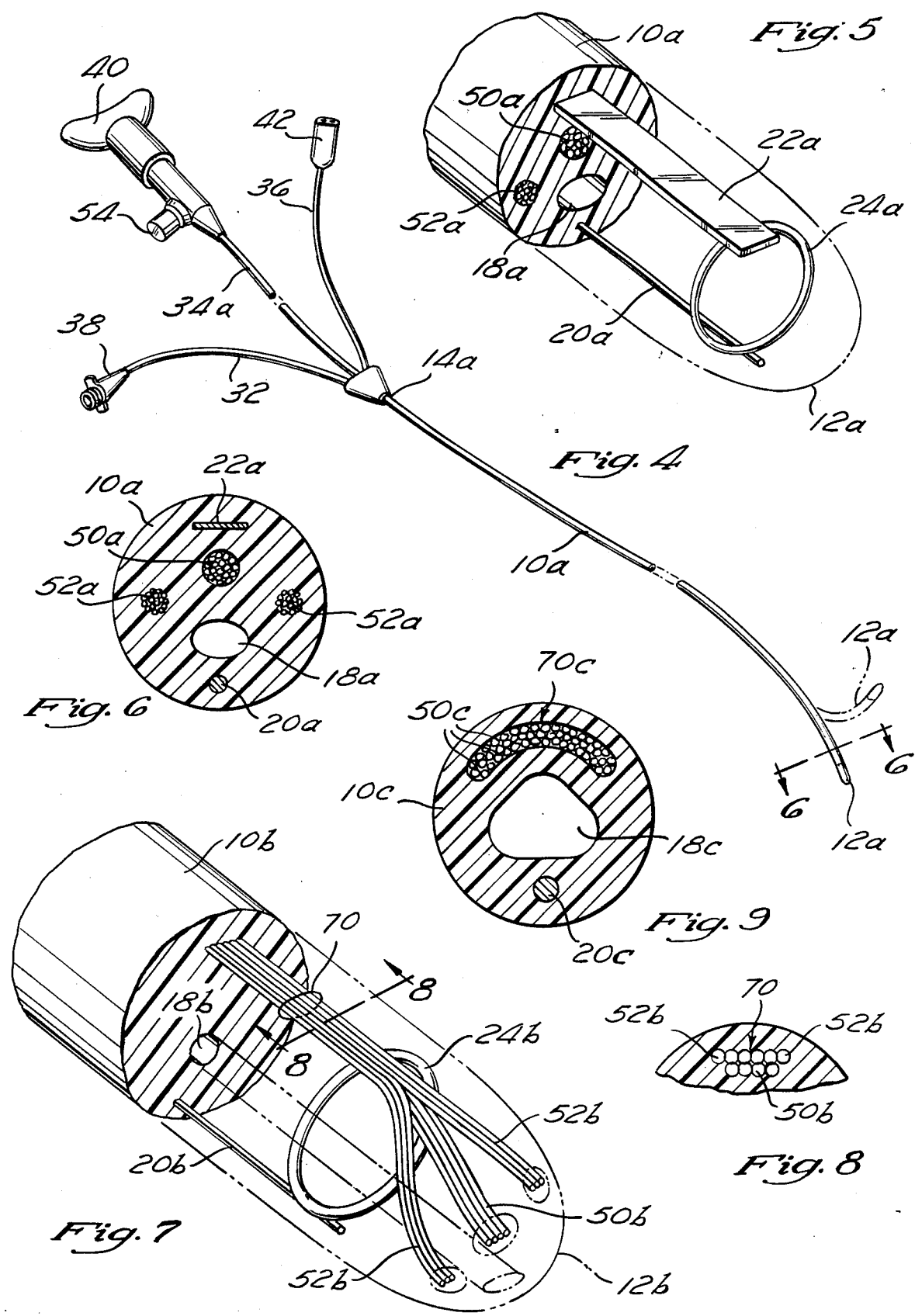

DEVICE FOR GUIDING MEDICAL CATHETERS AND SCOPES

BACKGROUND OF THE INVENTION

The present invention relates generally to the medical arts and more particularly to an improved means for guiding various catheters, cannulas, scopes, and the like during insertion and/or advancement thereof into various anatomical passages, tracts, cavities, vessels, and/or other structures of the body.

The prior art includes numerous catheters, cannulae, and tubular endoscopic devices having distal ends which are adapted for steering or manipulation. Examples of such devices are set forth in U.S. Pat. Nos. 3,890,977 (Wilson), 4,033,331 (Guss et al.), 4,543,090 (McCoy), 4,601,705 (McCoy), and 4,758,222 (McCoy).

Notably, U.S. Pat. Nos. 4,543,090, 4,601,705, and 4,758,222 describe a catheter having a steerable and/or bendable distal end. Such catheter incorporates known temperature-activated memory elements made of materials such as titanium-nickel alloys having heat-activated "mechanical memory". Each such temperature-activated memory element has a first "preset" shape and a second "straightened" shape. Such temperature-activated memory elements are initially disposed within the catheter in their straightened configuration. However, when electrically heated to a predetermined transitional temperature, the memory elements will undergo bending, thereby effecting the desired bending of the distal end of the catheter. A control system is provided for controlling current flow to the temperature-activated memory elements Such control systems include a power supply source (AC or DC) in conjunction with a controlling or steering means (e.g. a "joy stick", tactile membrane switch or ball controller) for triggering selective heating, and hence selective directional bending, of the various temperature-activated memory elements disposed within the distal end of the catheter.

Although such steerable/bendable catheters and scopes of the prior art may indeed incorporate means for bending or directing the distal portions thereof, many of these prior art devices are expensive to manufacture and/or less than optimal for certain medical applications. Accordingly, there remains a need in the art for a practically applicable, steerable or directable cannula, catheter or scope which may be inexpensively and reproduceably manufactured.

SUMMARY OF THE INVENTION

The present invention overcomes some or all of the shortcomings of the prior art by providing a "bending assembly" positionable within a flexible device, such as a catheter, cannula, or scope, and operative to effect controlled, reproducible bending of the distal portion thereof.

The "bending assembly" of the present invention comprises (a) a contractile member, (b) a bendable support member, and (c) a connecting member. The contractile member (e.g. contractile wire, fiber, coil, strip, etc.) is operative to undergo axial shortening upon application of an electrical current thereto. The bendable support member comprises a bendable segment of ribbon-like metal, plastic, or other material(s) positioned in spaced relation to the contractile member. The connecting member serves to connect one or more points of the contractile member to the bendable support member such that axial shortening of the contractile member will cause the bendable support member to bend in the direction of the contractile member.

The above-described bending assembly is sized and configured to be positioned within the distal portion of a flexible catheter, cannula, scope, or the like. Additionally, means (e.g. wires leading to a separate current source) are provided for periodically passing electrical current through the contractile member. Thus, when current is passed through the contractile member, the axial shortening of the contractile member and the accompanying movement of the bendable support member will cause the body of the catheter, cannula, scope, or the like to bend accordingly.

In embodiments wherein the bending assembly of the present invention is incorporated into an endoscopic instrument, the "bendable support member" element of the bending assembly may be formed of some or all of the light transmitting and/or image transmitting fibers which normally run through the flexible elongate body of the instrument. Thus, by utilizing the existing structures within the body of the instrument, it is possible to eliminate the need for the placement of an extraneous metal ribbon, plastic ribbon, Or other separate bendable support structure which comprises part of the bending assembly of the present invention.

When the electrical current is removed from the contractile wire, the bending assembly resumes its original configuration, thereby permitting the catheter, cannula, scope, or the like to return to its original, non-bent configuration. Thus, it is preferable that the bendable support member of the bending assembly be formed of bendable material having sufficient memory or resilience to return to its original configuration as the contractile wire re-expands or returns to its original length.

Specific objects and advantages of the invention will become apparent to those skilled in the art upon reading and understanding the following detailed description and the accompanying drawings.

BRIEF DESCRIPTION OF THE DRAWINGS

FIG. 1 is a perspective external view of an intravascular catheter in accordance with the present invention;

FIG. 2 is a cutaway perspective view of the distal portion of the intravascular catheter of FIG. 1;

FIG. 3 is a cross-sectional view through line 3—3 of FIG. 1;

FIG. 4 is a perspective view of a preferred angioscope in accordance with the present invention;

FIG. 5 is a outaway perspective view of the distal Portion of the angioscope of FIG. 4;

FIG. 6 is a cross-sectional view through line 6—6 of FIG. 4;

FIG. 7 is a cutaway perspective view of the distal tip of a first alternative embodiment of an angioscope of the present invention;

FIG. 8 is a cross-sectional view through line 8—8 of FIG. 7; and

FIG. 9 is a cross-sectional view of a second alternative embodiment of an angioscope of the present invention.

DETAILED DESCRIPTION OF PREFERRED EMBODIMENTS

The following detailed description and the accompanying drawings are intended for purposes of describing and illustrating presently preferred embodiments of the invention and are not intended to limit the scope of the invention in any way.

The accompanying drawings show (a) a preferred vascular catheter of the present invention in FIGS. 1-3 and (b) several preferred scopes of the present invention in FIGS. 4-9.

Referring to the drawings, FIG. 1 shows an intravascular catheter 10 having a distal end 12 and a proximal end 14. A connecting hub 16 is formed on the proximal end of the catheter. As shown in the views of FIGS. 2 and 3, a hollow working lumen 18 extends axially through the center of the catheter from the proximal end thereof to the distal end. Such lumen 18 opens through the distal end of the oatheter. The lumen 18 is fluidly consistent with the inner bore of connecting hub 16, thereby permitting fluid infusion and/or withdrawal through the body of the catheter 10 by way of a solution administration line, syringe, or other device attached to connecting hub 16.

A contractile wire 20 is disposed within the distal portion (e.g. the distal-most 5-10 cm) of the catheter 10. The contractile wire 20 is connected to a power source by way of at least one connector wire (not shown) which extends through the body of the catheter.

A preferred contractile wires formed of nickel-titanium alloy which undergoes axial shortening when electric current is passed therethrough. Such wire is available commercially, such as BioMetal ™, Toki Corporation, Tokyo, Japan. Because the contractile wire 20 is positioned on one side of the catheter body 10, such longitudinal shortening or contraction of the wire 20 will cause the distal portion of the oatheter to bend to the side (see dotted lines—FIG. 1) on which the wire 20 is positioned.

However, in some embodiments, the material of which the body of catheter 10 is made and/or the manner in which the contractile wire 20 is positioned within the catheter 10 will result in undesirable puckering or compaction of the catheter body and/or slippage of the wire 20 as the wire 20 undergoes contraction. Thus, in order to prevent such compaction, puckering, or slippage, it is preferable that bendable support member 22 be positioned within the catheter 10, in substantially parallel relation to the contractile wire 20.

In the preferred embodiment shown, the bendable support member 22 comprises a thin, flat ribbon-like member of metal or plastic. This ribbon-like member will bend in the direction of the contractile wire 20 when the contractile wire 20 shortens. Additionally, this preferred ribbon-like member possesses sufficient resilience or memory to repeatedly return to its original straight configuration after undergoing the desired bending in response to shortening of the contractile wire. While this ribbon-like support member 22 has been found to be desirable, it is to be appreciated that many other bendable support members may be made of many other materials and/or configurations and still achieve the desired support function carried out by the ribbon-like member shown. In some applications it may be possible to merely increase the size, cross-sectional thickness, density, rigidity, or some other aspect of a portion of the catheter body adjacent or near the contractile member or wire 20, thereby achieving formation of the bendable support member by merely altering, strengthening, stiffening, or building up a portion of the catheter body rather than by incorporating an extraneous object, such as a metal or plastic ribbon thereinto.

One or more connecting members 24 serve to physically connect the bendable support member 22 to the contractile wire 20 so as to form a unitary "bending assembly" or structure within the distal portion of the catheter. In the preferred embodiment shown, the connecting member 22 comprises a wire ring or loop. The wire loop is welded or otherwise attached, on opposite sides thereof, to the contractile wire 20 and the bendable support member 22, thereby forming the unitary bending assembly of the present invention.

The formation of a unitary bending assembly in accordance with the present invention serves to ensure that the entire distal portion of the catheter will undergo the desired bending in response to axial contraction of the contractile wire 20. The provision of such unitary bending assembly or structure further serves to ensure that the distal portion of the catheter will bend reproduceably time after time without substantial variation in the degree and/or direction of bending as may occur if the individual contractile wire 20 becomes separated from the catheter body 10 and/or undergoes a change in positioning therein.

The bendable support member 22 and connector member 24 may be formed of and/or incorporate electrically conductive materials so as to give rise to an electrical circuit within the body of the catheter. For example, in this preferred embodiment a first electrically conductive wire (not shown) extends through the body of the catheter !0 and is connected to the proximal end of contractile wire 20. A second electrically conductive wire (not shown) also extends through the catheter body 10 and is connected to the proximal end of the bendable support member 22. In this preferred embodiment, the bendable support member 22, the connecting member 24, and the contractile wire 20 are all formed of electrical conductive materials. Thus, when a positive charge is applied to the first electrical wire and ground applied to the second electrical wire, current will flow through the contractile wire 20, through the connecting member 24, through support member 22, and back to the proximal end of the catheter by way of the second wire. By such arrangement, the desired bending of the catheter tip may be achieved by periodically applying a positive charge to the first wire.

A plug or jack 30 extends from the catheter body !0 and is connected to the first and second electrical wires (not shown) to provide for simple interconnection of an attendant current source or controller to the catheter. Such current source or controller may include a switch or any other feasible means for periodically applying electrical current through the body of the catheter to the bending assembly positioned near the distal tip thereof.

Accordingly, the cardiovascular oatheter shown in FIGS. 1-3 may be initially inserted into a blood vessel and subsequently guided through various branches, furcations, sinuses, side vessels, or other structures of the vasculature, as desired, by periodically passing current through the bending assembly and/or the contractile wire 20 positioned within the distal portion of the catheter, thereby causing bending of the distal portion of the catheter. Controlled periodic bending or curving of the distal portion of the oatheter will allow the catheter to be advanced into specific side vessels, branches, furcations, and the like.

Although, in this embodiment, the catheter is capable of bending in only one direction, those skilled in the art will understand and appreciate that multi-directional guidance and positioning of the catheter may be easily attained by simply spinning or turning the catheter body 10 as it is advanced through the desired side vessels, branches, or furcations of the vasculature. Of course, radiographic assistance may be employed to enable the operator to periodically or continuously view the position of the catheter tip. Additionally, a plurality of gauge marks 32 may be formed on the catheter body to allow the operator to determine how much of the catheter 10 has been inserted. Such gauging marks 32 may be formed only on one side of the catheter body 10 so as to also serve as reference points by which the operator may determine the rotational orientation of the distal cannula tip 12.

Although the catheter shown in FIGS. 1-3 has been described as a "cardiovascular catheter" intended for insertion into blood vessels and the like, it will be appreciated that the catheter shown in FIGS. 1-3 and various foreseeable modifications thereof may have other uses as well. For example, in some endoscopic instruments and the like it is not feasible to build tip directing/bending components into the scope itself as such may interfere with other necessary elements and/or components of the scope and/or may require an undesirable narrowing of any working lumen of the scope. In such applications wherein the scope or other instrument lacks sufficient distal tip bending capability in itself, desirable steerability or guidability may be achieved by initially inserting a directable catheter 10 of the type shown in FIGS. 1-3 axially through an inner lumen of the endoscope or other instrument to a point where the distal portion of the catheter 10 is positioned within the distal portion of the non-guidable endoscope or instrument. Controlled manipulation and bending of the catheter 10 will then bring about corresponding manipulation and bending of the distal portion of the endoscope or instrument. Thus, the inserted catheter 10 may be utilized as a means for guiding and manipulating an otherwise non-guidable endoscopic device. After the endoscope or instrument has been guided and advanced to its desired position, the catheter 10 may be proximally withdrawn and removed, thereby leaving the lumen of the endoscopic device open and free for other uses (e.g. fluid infusion, lavage, removal of biopsy samples, etc.).

In addition to the oatheter embodiment shown in FIGS. 1-3, the bending assembly (i.e. the contractile wire 20, bendable support member 22, and connecting member 24 as described above) may be incorporated directly into the distal portion of various endoscopic devices. For example, FIGS. 4-6 show an angioscope comprising an elongate flexible body 10a having a distal end 12a and a proximal end 14a. A plurality of image transmitting fibers 50 extend longitudinally through the flexible body 10a and consistently longitudinally through flexible member 34a so as to permit transmission of a visual image from an image-receiving apparatus or lens mounted on the distal tip 12a of the flexible body 10a to an imaging means positioned on the extreme proximal end of the device. Such imaging means may comprise any known means for projecting and/or viewing a visual image. For example, as shown in FIG. 4 an eyepiece 40 may be mounted on the proximal end of the scope. Additionally and/or alternately connectors and/or other attachments may be provided for connecting the scope to a separate camera and/or video monitor, or a small camera may be mounted directly on the proximal end of the scope.

Additionally, a plurality of light transmitting fibers 52a extend longitudinally through the flexible body 10a and continuously longitudinally through flexible member 34a so as to transmit or carry light from light source 54 to one or more illuminating ports (not shown) located on the distal tip 12a of the flexible body 10a. A working lumen 18a also extends longitudinally through the flexible body 10a opening at or near the distal tip 12a thereof. Such working lumen 18a extends consistently longitudinally through flexible member 32. A female Leur-type connector 38 is mounted on the extreme proximal end of flexible member 32 so as to permit slidable and/or interlocking connection of a solution administration line, syringe, or other device so as to effect desired infusion and/or withdrawal of fluids through the working lumen 18a.

The "bending assembly" disposed within the distal portion of the angioscope shown in FIGS. 4-6 is formed of the same components and constructed in the same manner as the bending assembly described above with respect to the catheter embodiment shown in FIGS. 1-3 (i.e. the contractile wire 20a, the bendable support member 22a, and the connecting member 24a).

To facilitate controlled triggering of the "bending assembly" in these scopes, at least first and second electrical wires (not shown) extend from plug member 42 through the flexible member 36 and longitudinally through the flexible body 10a so as to provide for passage of an electrical current through at least the contractile wire 20 component of the bending assembly. The first electrical wire (not shown) may be connected to the proximal end of contractile wire 22a and the second electrical wire (not shown) may be connected to the proximal end of bendable support member 20a. A power source or controller is attached to plug 42 so as to permit application of positive current of the first wire and to ground the second wire, thereby completing a circuit through the contractile wire 20 causing axial shortening of the wire 20a with resultant bending of the distal portion of the angioscope (see dotted lines on FIG. 4).

FIGS. 7 and 8 show an alternative angioscope embodiment of the present invention wherein the above-described bendable support member 22, 22a is replaced by a bundle or packet of optical fibers 70. Such optical fiber bundle 70 extends longitudinally through the catheter body 10b such that at least a portion thereof lies in generally parallel relationship to the contractile wire 20b. The fiber bundle 70 which replaces the above-described bendable support member 22, 22a consists of both image transmitting fibers 50b and light transmitting fibers 52b. Such fibers 50b, 52b are arranged in a packet or bundle as shown in the cross-sectional view of FIG. 8. The individual fibers 50b, 52b within packet 70 may be bound together by an adhesive substance or may otherwise be held in fixed relation so as to form a bendable structure having the desired structural and skeletal rigidity necessary to carry out the same functions described above with respect to the bendable support member 22, 22a. It is by this structural and skeletal function that the fiber packet 70 of the scope device may be configured and utilized to take the place of the above-described bendable support member 22, 22a. The connecting member or wire loop 24b serves to connect the contractile wire 20b to the fiber bundle 70. Distal to the wire loop 24b, the fiber bundle 70 separates into groups of light transmitting fibers 52b which extend to light output ports and a group of image transmitting fibers 50b which extends to an image receiving lens or opening located on the distal tip 12b of the cannula body 10b.

In another alternative angioscope embodiment shown in FIG. 9, the fiber packet 70c is similar in composition and function as the fiber bundle 70 of the embodiment of FIGS. 7-8, however, disposed within an arcuate or sausage-shaped lumen as shown. Additionally, in the alternative embodiment shown in FIG. 9, the working lumen 18c is shaped in a three-sided configuration as shown. The incorporation of (a) the arcuate or sausage-shaped fiber bundle 70c and (b) the three-sided working lumen 18c provides a catheter which exhibits the desired ability to bend near its distal tip. The arcuate or sausage-shaped fiber bundle 70c may comprise an arcuate or sausage-shaped lumen which extends axially through the flexible body 10c with the plurality of light transmitting and image transmitting fibers disposed axially therein.

Although the invention has been described herein with reference to presently preferred embodiments thereof, it will be appreciated by those skilled in the art that numerous additions, deletions, and modifications may be made to such preferred embodiments without departing from the spirit and scope of the invention. For example, the above-described preferred embodiments are limited to use of the novel bending assembly within (a) a standard catheter in the nature of a cardiovascular catheter and (b) a small diameter scope in the nature of an angioscope. It is to be understood, however, that the novel bending assembly (i.e. contractile wire, bendable support member, and connecting member) of the present invention may be incorporated into many different types of devices wherein guidability is desired, including but not limited to cardiovascular catheters, other catheters, angioscopes, cystoscopes, laparoscopes, arthroscopes, colonoscopes, gastroscopes, etc. Additionally, the contractile member or contractile wire element of the bending assembly need not be specifically configured as a wire but, rather, may be in the form of a flat ribbon, coil, fibers, or other contractile configuration. Accordingly, it is intended that all such additions, deletions, and modifications be included within the scope of the following claims and the equivalents thereof.

What is claimed is:

1. An assembly positionable within a flexible cannula to cause bending thereof, said assembly comprising:
    a contractile member operative to undergo axial shortening upon application of an electrical current thereto;
    a bendable support means positioned adjacent to and in spaced relation to said contractile member
    a connecting member connecting said contractile member to said bendable support member; and
    said contractile member, said bendable support member, and said connecting member being sized, configured, and assembled in such manner as to be positionable within said flexible cannula such that the axial shortening of the contractile member will result in bending of the bendable support member with concomitant bending of the flexible cannula in conformance therewith.

2. The assembly of claim 1 wherein said contractile member comprises a nickel-titanium alloy which undergoes axial shortening when heated as by passage of an electrical current therethrough.

3. The assembly of claim 1 wherein said contractile member comprises a wire.

4. The assembly of claim 3 wherein said wire is approximately 0.006 inch in diameter and approximately 3 inches in length.

5. The assembly of claim 1 wherein said bendable support member is approximately 3 inches in length.

6. The assembly of claim 1 wherein said bendable support member comprises a ribbon-like segment of metal.

7. The assembly of claim 1 wherein said bendable support member comprises a ribbon-like segment of plastic.

8. The assembly of claim 1 wherein said connecting member comprises at least one wire member connected to and extending between said contractile wire and said bendable support member.

9. The assembly of claim 8 wherein said at least one wire comprises a generally circular wire loop.

10. The assembly of claim 1 wherein said contractile wire, said bendable support member, and said connecting member are all formed of electrically conductive materials and wherein a first electrical wire is connected to said contractile wire and a second electrical wire is connected to said bendable support member such that application of a positive charge to said first electrical wire and a negative charge to said second electrical wire will give rise to a current flow through said assembly as to cause axial shortening of said contractile wire and resultant bending of said bendable support member.

11. A guidable catheter for insertion into anatomical structures of the body, said catheter comprising:
    a flexible sheath having first and second longitudinal ends and a hollow lumen extending axially therethrough;
    a bending assembly formed within said flexible sheath, near the distal end thereof, said bending assembly comprising:
        a contractile member operative to undergo axial shortening upon application of an electrical current thereto;
        a bendable support member positioned adjacent to and in spaced relation to said contractile wire;
        a connecting member connecting said contractile wire to said bendable support member;
        said contractile member, said bendable support member, and said connecting member being sized, configured, and assembled in such manner as to be positionable within said flexible cannula such that the axial shortening of the contractile member will result in bending of the bendable support member with concomitant bending of the flexible cannula in conformance therewith; and
        a means for providing an electrical current to said contractile wire so as to cause said axial shortening of said contractile wire with resultant bending of said bendable support member and the distal portion of said oatheter.

12. The oatheter of claim 11 wherein said contractile member comprises a wire.

13. The catheter of claim 11 wherein said wire comprises a nickel-titanium alloy which undergoes axial shortening when heated as by passage of an electrical current therethrough.

14. The catheter of claim 12 wherein said contractile wire is approximately 0.006 inch in diameter and approximately 3 inches in length.

15. The catheter of claim 11 wherein said bendable support member is approximately 3 inches in length.

16. The catheter of claim 11 wherein said bendable support member comprises a ribbon-like segment of metal.

17. The catheter of claim 11 wherein said bendable support member comprises a ribbon-like segment of plastic.

18. The catheter of claim 11 wherein said connecting member comprises at least one wire member connected to and extending between said contractile member and said bendable support member.

19. The catheter of claim 18 wherein said at least one wire comprises a generally circular wire loop.

20. The catheter of claim 11 wherein said contractile member, said bendable support member, and said connecting member are all formed of electrically conductive materials and wherein a first electrical wire is connected to said contractile wire and a second electrical wire is connected to said bendable support member such that application of a positive charge to said first electrical wire and a negative charge to said second electrical wire will give rise to a current flow through said assembly as to cause axial shortening of said contractile wire and resultant bending of said bendable support member.

21. The guidable catheter of claim 11 wherein said bendable support member comprises an integral portion of said flexible sheath.

22. The guidable catheter of claim 21 wherein said bendable support member comprises a strengthened region within said flexible sheath, said strengthened region being more rigid than the remainder of said sheath yet sufficiently bendable to achieve the function of said bendable support member.

23. An endoscope having a bendable distal portion, said endoscope comprising:
a flexible elongate body having proximal and distal longitudinal ends;
at least one image transmitting fiber extending longitudinally through said elongate body so as to effect transmission of a visual image from the distal end of said elongate body to the proximal end of said elongate body;
at least one light transmitting fiber extending longitudinally through said elongate body so as to carry illuminating light from the proximal end of said elongate body to the distal end of said elongate body;
at least one means for providing light energy to said light transmitting fiber;
an imaging means positioned on the proximal end of said elongate body for receiving and viewing visual images transmitted through said at least one image transmitting fiber;
a bending assembly positioned near the distal end of said elongate body, said bending assembly comprising:
a contractile member operative to undergo axial shortening upon application of an electrical current thereto;
a bendable support means positioned adjacent to and in spaced relation to said contractile wire;
a connecting member connecting said contractile wire to said bendable support member;
said contractile wire, said bendable support member, and said connecting member being sized, configured, and assembled in such manner as to be positionable within said flexible cannula such that the axial shortening of the contractile wire will result in bending of the bendable support member with concomitant bending of the flexible cannula in conformance therewith; and
a means for providing an electrical current to said contractile wire so as to cause said axial shortening of said contractile wire with resultant bending of said bendable support member and the distal portion of said catheter.

24. The endoscope of claim 23 wherein said contractile member comprises a wire.

25. The endoscope of claim 24 wherein said contractile wire is approximately 0.006 inch in diameter and approximately 3 inches in length.

26. The endoscope of claim 23 wherein said contractile member comprises a nickel-titanium alloy which undergoes axial shortening When heated as by passage of an electrical current therethrough.

27. The endoscope of claim 23 wherein said bendable support member is approximately 3 inches in length.

28. The endoscope of claim 23 wherein said bendable support member comprises a ribbon-like segment of metal.

29. The endoscope of claim 23 wherein said bendable support member comprises a ribbon-like segment of plastic.

30. The endoscope of claim 23 wherein said connecting member comprises at least one wire member connected to and extending between said contractile wire and said bendable support member.

31. The endoscope of claim 30 wherein said at least one wire comprises a generally circular wire loop.

32. The endoscope of claim 23 wherein said contractile member, said bendable support member, and said connecting member are all formed of electrically conductive materials and wherein a first electrical wire is connected to said contractile member and a second electrical wire is connected to said bendable support member such that application of a positive charge to said first electrical wire and a negative charge to said second electrical wire will give rise to a current flow through said assembly as to cause axial shortening of said contractile member and resultant bending of said bendable support member.

33. The endoscope of claim 23 wherein said bendable support member comprises portions of said at least one image transmitting fiber positioned in spaced relation to said contractile member and being connected to said contractile wire by said connecting member so as to achieve the function of said bendable support member.

34. The endoscope of claim 23 wherein said bendable support member comprises portions of said at least one light transmitting fiber positioned in spaced relation to said contractile member and being connected to said contractile member by said connecting member so as to achieve the function of said bendable support member.

35. The endoscope of claim 34 wherein the unitary bundle of fibers is generally rectangular in cross-sectional configuration.

36. The endoscope of claim 34 wherein the unitary bundle of fibers is generally arcuate in cross-sectional configuration.

37. The endoscope of claim 23 wherein said bendable support member comprises portions of said at least one light transmitting fiber positioned in spaced relation to said contractile wire and being connected to said contractile wire by said connecting member so as to achieve the function of said bendable support member.

38. The endoscope of claim 37 wherein the portions of said light transmitting fibers which form the bendable support member comprise generally elongate fibers positioned in parallel relation to one another and affixed in a unitary bundle of sufficient mass to carry out the function of said bendable support member.

39. The endoscope of claim 38 wherein the unitary bundle of fibers is generally rectangular in cross-sectional configuration.

40. The endoscope of claim 39 wherein the unitary bundle of fibers is generally arcuate in cross-sectional configuration.

41. The endoscope of claim 23 wherein said bendable support member comprises portions of said at least one image transmitting fiber and said at least one light transmitting fiber positioned in spaced relation to said contractile member and being connected to said contractile member by said connecting member so as to achieve the function of said bendable support member.

42. The endoscope of claim 23 wherein said imaging means comprises an eyepiece.

43. The endoscope of claim 23 wherein said imaging means comprises a camera.

44. The endoscope of claim 23 wherein said imaging means comprises a connector for attachment to said camera.

45. The endoscope of claim 23 wherein said imaging means comprises a connector for attachment to a video monitor.

46. The endoscope of claim 21 wherein said bendable support member comprises an integral portion of said flexible sheath.

47. The endoscope of claim 46 wherein said bendable support member comprises a strengthened region within said flexible sheath, said strengthened region being more rigid than the remainder of said sheath yet sufficiently bendable to achieve the function of said bendable support member.

* * * * *